United States Patent [19]

Belsole

[11] Patent Number: 4,696,821

[45] Date of Patent: Sep. 29, 1987

[54] TRANSDERMAL DELIVERY SYSTEM FOR ADMINISTRATION OF NITROGLYCERIN

[75] Inventor: Susan C. Belsole, Chester, N.J.

[73] Assignee: Warner-Lambert Company, Morris Plains, N.J.

[21] Appl. No.: 540,249

[22] Filed: Oct. 11, 1983

[51] Int. Cl.$^4$ .............................................. A61F 13/00
[52] U.S. Cl. ...................................... 424/448; 424/449
[58] Field of Search ................... 424/28, 80, 298, 449, 424/448

[56] References Cited

U.S. PATENT DOCUMENTS

| | | | |
|---|---|---|---|
| 3,063,900 | 11/1962 | Winsor | 424/298 |
| 3,214,338 | 10/1965 | Ehrlich | 424/80 |
| 3,287,222 | 11/1966 | Larde et al. | 424/80 |
| 3,972,995 | 8/1976 | Tsuk et al. | 424/28 |
| 4,210,633 | 7/1980 | Takruri et al. | 424/80 |

FOREIGN PATENT DOCUMENTS

| | | |
|---|---|---|
| 1135625 | 11/1982 | Canada . |
| 13606 | 7/1980 | European Pat. Off. . |
| 58-18316 | 2/1983 | Japan . |
| 83/00093 | 1/1983 | PCT Int'l Appl. . |
| 1127881 | 3/1976 | United Kingdom . |
| 2073588 | 10/1981 | United Kingdom . |
| 2081582 | 2/1982 | United Kingdom . |

OTHER PUBLICATIONS

C.A. 94:20412e, Polymeric Diffusion Matrix and Drug Device Comprising said Matrix.

*Primary Examiner*—Alan Siegel
*Attorney, Agent, or Firm*—Ronald A. Daignault

[57] ABSTRACT

A transdermal delivery system for the administration of nitroglycerin for the treatment of heart disease comprising a nitroglycerin water-soluble polyvinylpyrrolidone polymer film coated on one surface of aluminum foil, the uncoated side of said aluminum foil mounted on the adhesive side of adhesive tape having dimensions larger than said aluminum foil is described.

9 Claims, No Drawings

TRANSDERMAL DELIVERY SYSTEM FOR ADMINISTRATION OF NITROGLYCERIN

BACKGROUND OF THE INVENTION

It is known that nitroglycerin is pharmaceutically useful in the treatment or prevention of angina pectoris, myocardial infarction paroxysm, and cardiac insufficiency.

Among internal treatments for ischemic heart disease is vasodilator therapy in which nitroglycerin is used as a coronary vasodilator. Its effects include dilation of the coronary artery, releasing contraction of the coronary artery and dilation of collateral and resistance vessels thereby increasing the oxygen supply to the ischemic area of cardiac muscle. It is also known that nitroglycerin has effects such as dilation of arteries and reduction of blood pressure throughout the body (thereby reducing the load applied to the heart), dilation a sublingual tablet or as an ointment.

Sublingual tablets are generally used for the treatment of paroxysm due to angina pectoris but the duration of effectiveness is rather short, for instance 20 to 30 minutes.

When prolongeday be up to four to eight hours.

The ointment is generaly applied using a scaled parchment paper applicator which may be for instance 6 cm×9 cm in size. The amount of ointment applied is generally the maximum that can be tolerated without the onset of headache, this being a symptom of undesirable side effects. For instance 0.35 g ointment (containing 7.5 mg nitroglycerin) may be applied to the frontal chest skin and further amounts of 0.35 g until headache develops which shows the amount is then too great. Generally, the amount is from 0.7 to 1.5 g (containing 14 to 30 mg nitroglycerin) and the ointment is generally applied over 200 cm$^2$ or more of the frontal chest skin.

To prevent evaporation of nitroglycerin and to prevent staining of clothes, the ointment is generally covered with a plastic film fixed to the skin by adhesive tapes.

The administration of ointment is thus rather inconvenient. It is difficult to determine the exact amount to be applied, and its application and removal can be messy.

Recently, three one-a-day type transdermal nitroglycerin (NTG) delivery systems in the form of patches were developed for controlled administration of nitroglycerin. These patches overcome the inherent problems of the ointment i.e., accuracy of dose, application, and staining. In addition, they release nitroglycerin at a uniform rate over a 24 hour period.

Belgian Pat. No. 893,394 describes a membrane-controlled delivery system for NTG. Materials and manufacturing for this device are complicated and costly. U.S. Pat. Nos. 4,336,243 and 4,291,015 describe matrix-controlled delivery systems. These are both bulky and inefficient requiring a wide perimeter of adhesive to insure intimate skin contact.

In addition, all three patches require a large excess of NTG to maintain a driving force for penetration.

Goodhart, et al., J Pharm. Sci. 65, No. 10, 1466 (1976) described the stabilization of compressed NTG tablets with polyvinylpyrrolidone (PVP). It was observed that the volatility and subsequent migration of the NTG was retarded with addition of PVP. European Pat. No. 054,279 describes the use of water-insoluble PVP crosslinked or copolymerized with acrylic or vinyl esters to provide a hydrophobic matrix system for controlled release of NTG. This matrix also reduces the drug's volatility. The present invention relates to the use of a nitroglycerin water soluble polyvinylpyrrolidone complex as both film-former and rate-controlling mechanism for the transdermal delivery of NTG.

SUMMARY OF THE INVENTION

The present invention provides a transdermal delivery system for the administration of nitroglycerin and more specifically, provides a simple nitroglycerin tape which is conveniently applied to the skin and is no more obtrusive than a common adhesive strip.

The tape comprises a polyvinylpyrrolidone film containing nitroglycerin, plasticizers and solvents for the nitroglycerin. The film is coated on an aluminum strip and said strip is mounted on an adhesive strip and covered with nonstick paper backing. The rate of release can be adjusted by appropriate choice of polyvinylpyrrolidone concentration.

In addition, the rate-controlling mechanism is such that higher blood levels can be expected from a surface area equivalent to commercially available products.

The present invention also includes a nitroglycerin containing polymer film for coating on the above tape and a method for treating angina pectoris by applying to the skin of a mammal suffering therefrom the above tape containing a nitroglycerin containing polymer film.

DESCRIPTION OF THE DETAILED EMBODIMENTS

The present invention provides a transdermal delivery system for the administration of nitroglycerin for the treatment of heart disease comprising a nitroglycerin water-soluble polyvinylpyrrolidine polymer film coated on one surface of aluminum foil. The uncoated side of said aluminum foil mounted on the adhesive side of adhesive tape having dimensions larger than said aluminum foil. The coated aluminum foil mounted on adhesive tape is applied to the body surface of a patient suffering from heart disease and specifically angina pectoris, whereby the film coated surface of the aluminum foil and the adhesive side of the adhesive tape are in intimate contact with the patient's skin.

Said coated aluminum foil may be made by preparing a nitroglycerin polyvinylpyrrolidone solution, spreading said solution on an aluminum foil to form a film, and allowing it to dry.

Said nitroglycerin polyvinylpyrrolidine solution is prepared by dissolving nitroglycerin in a suitable solvent and further adding plasticizers and polyvinylpyrrolidone with stirring until complete solution is attained.

The polyvinylpyrrolidones used to form the film are water-soluble and can range in molecular weight from 10,000 to 360,000. The preferred molecular weight is 360,000. The ratio of PVP to NTG can vary from 2:1 to 10:1 depending upon the molecular weight of the polymer chosen and the release rate desired. An increase in the PVP/NTG ratio will generally decrease the rate of release.

Plasticizers compatible with PVP and NTG may be chosen from a list including glycerin, PEG 400, propylene glycol, sorbitol, water soluble lanolin oils, diethylene glycol, butylene glycol, acetylated lanolins, or a mixture thereof. Concentrations of plasticizers in the film alone or in combination range from 15–40%, preferably 22%.

Solvents for NTG may include octlyhydroxystearate, octyl palmitate, isopropyl myristate, isopropyl palmitate, mineral oil, lanolin alcohol, dimethicone fluid or capric/caprylic triglycerides. Solvent concentration in the film ranges from 5–25% depending on the amount of NTG present.

The plasticizer chosen may also act as a solvent for NTG as, for instance, acetylated lanolin, propylene glycol or water-soluble lanolin. When lanolin derivatives are used, the absorption of NTG will be improved. While the rate of release is controlled mainly by the choice of PVP concentration, the solvents and plasticizers used will have some effect. A product of this type, because of its simplicity, is relatively easy to manufacture and assemble.

The film of the present invention can vary in size depending upon the dosage requirements of the patient. The NTG content of the film ranges from 10 mg to 30 mg but the preferred size is 2.5cm×4 cm containing 22.28 mg NTG.

The following examples are illustrative of the invention.

EXAMPLE 1

Preparation of Nitroglycerin Polyvinylpyrrolidone Solution: A 9.1% w/w solution of NTG in alcohol USP (26.37 g) was mixed with 58.63 ml of alcohol USP until a uniform solution was obtained. To this solution were added 1 g of PEG-75 lanolin oil, 1 g of octyl hydroxystearate and 3 g of glycerin USP. Polyvinylpyrrolidone, molecular weight 360,000 (5 g) was then added slowly and mixed until completely dissolved.

Assembly of Tape: Approximately 0.928 ml of the nitroglycerin polyils. The foil strip was then centered over the adhesive side of an adhesive strip measuring 5 cm×6.5 cm and pressed into place. A nonstick paper backing was applied to cover both foil strip and adhesive. The assembled tape was packaged in heat-sealable foil pouches.

EXAMPLE 2

A nitroglycerin polyvinylpyrrolidone solution was prepared following the method and materials of Example 1 except that 10 g of PVP, molecular weight 360,000, was added. The film was cast on foil, assembled and packaged as in Example 1.

EXAMPLE 3

A nitroglycerin polyvinylpyrrolidone solution is prepared following the method and materials of Example 1 except that 15 g of PVP, molecular weight 360,000, are added. The film is cast on foil, assembled, and packaged as in Example 1.

EXAMPLE 4

A nitroglycerin polyvinylpyrrolidone solution is prepared following the method and materials of Example 1 except that 3 g of PVP, molecular weight 360,000, are added. The film is cast on foil, assembled, and packaged as in Example 1.

EXAMPLE 5

Studies to determine the topical availability of nitroglycerin from the films were carried out in vitro using hairless mouse skin. Although in vitro permeation through hairless mouse skin is not an absolute quantitation of drug delivery through human skin, the rank order of formulations tested is usually the same. Thus, commercially available products whose in vivo performance is known may be used as standards when tested in vitro under the same conditions.

The data for the in vitro release of NTG from the films prepared in Examples 1 and 2 are set forth in the following table. Commercial standards used were a 2% NTG ointment and a transdermal delivery system of 10 cm² (TDDS).

| T (hours) | NTG Released (mcg/cm²)* | | | |
| --- | --- | --- | --- | --- |
| | Film Ex. 1 | Film Ex. 2 | 2% Ointment (1 mm thick) | TDDS 10 cm² |
| 1 | 0 | 0 | 10 | 7 |
| 2 | 25 | 10 | 30 | 45 |
| 4 | 60 | 50 | 65 | 85 |
| 8 | 175 | 130 | 140 | 135 |
| 12 | 330 | 220 | 210 | 190 |
| 16 | 510 | 320 | 275 | 245 |
| 20 | 680 | 420 | 335 | 290 |
| 24 | 850 | 525 | 390 | 340 |
| 30 | 1,090 | 675 | 470 | 410 |

*mean of eight determinations

Release from the ointment was linear with $T^{\frac{1}{2}}$ while both the films and the TDDS exhibit zero order release rates.

I claim:

1. A tape for transdermal delivery of nitroglycerin comprising nitroglycerin-containing pyrrolidone film coated on one surface of aluminum foil with the uncoated surface of said aluminum foil mounted on the adhesive strip wherein the dimensions of said adhesive strip are larger than said aluminum foil, and said film contains 10 to 30 mg nitroglycerin dissolved in a solvent selected from the group consisting of octyl hydroxystearate, octly palmitate, mineral oil, lanolin alcohol, dimethicone fluid and capric/caprylic triglyceride and 30–70% by weight water soluble polyvinylpyrrolidone of molecular weight 10,000 to 360,000 plasticized with a plasticizer selected from the group consisting of glycerin, PEG-400, propylene glycol, sorbitol, PEG-75 lanolin oil, diethylene glycol, sorbitol, PEG 75 lanolin oil, diethylene glycol, butylene glycol, acetylated lanolin and a mixture thereof.

2. A tape as claimed in claim 1 wherein said solvent concentration is from 5 to 25% by weight of the film and the plasticizer concentration is from 15 to 40% by weight of the film.

3. A tape as claimed in claim 2 wherein the nitroglycerin content is about 22.28 mg dissolved in a solvent selected from the group consisting of octly hydroxystearate, octly palmitate and lanolin alcohol, the polyvinylpyrrolidone concentration is 40 to 60% by weight of the film and the plasticizer is selected from the group consisting of glycerin, PEG-75 lanolin oil, propylene glycol, and a mixture thereof at a concentration of 20 to 35% by weight of the film.

4. A tape as claimed in claim 3 wherein about 22.28 mg of nitroglycerin is dissolved in octyl hydroxystearate at about 8% by weight of the film, and about 48% by weight of the film of polyvinylpyrrolidone of molecular weight of about 360,000 plasticized with PEG-75 lanolin oil and glycerin at a concentration of about 8% and about 24%, respectively by weight of the film.

5. A tape as claimed in claim 3 wherein about 22.28 mg of nitroglycerin is dissolved in octyl hydroxystearate at about 6% by weight of the film, and about 57% by weight of the film of polyvinylpyrrolidone of molecular weight of about 360,000 plasticized with PEG-75 lanolin oil and glycerin at a concentration of about 6% and about 17%, respectively, by weight of the film.

6. A tape as claimed in claim 4 or 5 wherein the film has dimensions of 2.5 cm×4 cm.

7. A nitroglycerin-containing polymer film for transdermal delivery of nitroglycerin comprising 10 to 30 mg of nitroglycerin dissolved in a solvent selected from the group consisting of octyl hydroxystearate, octyl palmitate, isopropyl myristate, isopropyl palmitate, mineral oil, lanolin alcohol, dimethicone fluid and capric/caprilic triglyceride, a water-soluble polyvinylpyrrolidone of molecular weight 10,000 to 360,000, and a plasticizer selected from the group consisting of glycerin, PEG-400, propylene glycol, sorbitol, PEG-75 lanolin oil, diethylene glycol, butylene glycol, acetylated lanolin and a mixture thereof.

8. A film as claimed in claim 7, wherein the nitroglycerin concentration is about 22.28 mg dissolved in 8% octyl hydroxystearate and polyvinylvinylpyrrolidone of molecular weight 360,000 comprises 48% by weight of the film plasticized with 8% PEG-75 lanolin oil and 24% of glycerin.

9. A film as claimed in claim 8, wherein the nitroglycerin is dissolved in 6% octyl hydroxystearate and polyvinylpyrrolidone of molecular weight 360,000 comprises 57% by weight of the film plasticized with 6% of PEG-75 lanolin oil and 17% of glycerin.

* * * * *